US009586991B2

(12) United States Patent
Cohen et al.

(10) Patent No.: US 9,586,991 B2
(45) Date of Patent: Mar. 7, 2017

(54) INHIBITORS OF IAP

(71) Applicant: GENENTECH, INC., South San Francisco, CA (US)

(72) Inventors: Frederick Cohen, San Francisco, CA (US); Lewis J. Gazzard, Belmont, CA (US); Vickie Hsiao-Wei Tsui, Burlingame, CA (US); John A. Flygare, Burlingame, CA (US)

(73) Assignee: GENENTECH, INC., South San Franscisco, CA (US)

( * ) Notice: Subject to any disclaimer, the term of this patent is extended or adjusted under 35 U.S.C. 154(b) by 0 days.

(21) Appl. No.: 14/974,140

(22) Filed: Dec. 18, 2015

(65) Prior Publication Data

US 2016/0102119 A1    Apr. 14, 2016

Related U.S. Application Data

(63) Continuation of application No. 14/269,739, filed on May 5, 2014, now Pat. No. 9,238,675, which is a continuation of application No. 13/733,244, filed on Jan. 3, 2013, now Pat. No. 8,716,236.

(60) Provisional application No. 61/582,760, filed on Jan. 3, 2012.

(51) Int. Cl.
| | |
|---|---|
| *A61K 38/48* | (2006.01) |
| *A61K 38/55* | (2006.01) |
| *C07K 14/81* | (2006.01) |
| *C07K 5/087* | (2006.01) |
| *C07K 5/09* | (2006.01) |
| *C07K 5/083* | (2006.01) |
| *C07K 5/08* | (2006.01) |
| *A61K 38/00* | (2006.01) |

(52) U.S. Cl.
CPC .............. *C07K 5/0812* (2013.01); *C07K 5/08* (2013.01); *C07K 5/0804* (2013.01); *C07K 5/0806* (2013.01); *C07K 5/0815* (2013.01); *A61K 38/00* (2013.01)

(58) Field of Classification Search
CPC ......... A61K 38/00; A61K 38/07; C07K 14/81
See application file for complete search history.

(56) References Cited

U.S. PATENT DOCUMENTS

| | | |
|---|---|---|
| 4,808,614 A | 2/1989 | Hertel |
| 7,244,851 B2 | 7/2007 | Cohen et al. |
| 8,044,209 B2 | 10/2011 | Charest et al. |
| 2006/0014700 A1 | 1/2006 | Cohen et al. |
| 2011/0015232 A1 | 1/2011 | Charest et al. |
| 2011/0077265 A1 | 3/2011 | Flygare et al. |

FOREIGN PATENT DOCUMENTS

| | | |
|---|---|---|
| GB | 2136425 A | 9/1984 |
| WO | 2008/045905 A1 | 4/2008 |
| WO | 2008/134679 A1 | 11/2008 |

OTHER PUBLICATIONS

International Search Report for PCT/US2013/020124 (Apr. 9, 2013).
Merck Index #4420, p. 809, 15th Ed., 2013.

*Primary Examiner* — Hasan Ahmed
*Assistant Examiner* — Kaipeen Yang
(74) *Attorney, Agent, or Firm* — Millen White Zelano and Branigan, PC; John Sopp; Anthony Zelano

(57) ABSTRACT

Novel inhibitors of IAP that are useful as therapeutic agents for treating malignancies and have the general formula I:

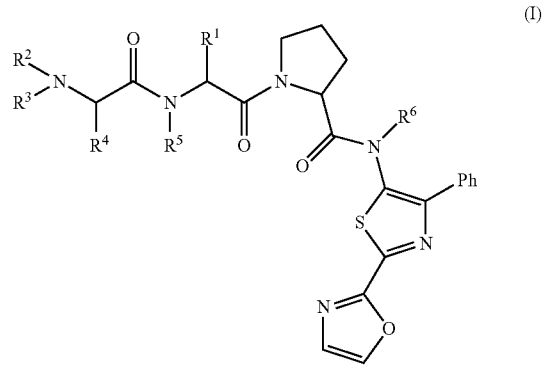

wherein $R^1$, $R^2$, $R^3$, $R^4$, $R^5$ and $R^6$ are as described herein.

10 Claims, 2 Drawing Sheets

SEQUENCE LISTING

```
<160> NUMBER OF SEQ ID NOS: 1

<210> SEQ ID NO 1
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Ser Ser His His His His His His Ser Ser Gly Leu Val Pro
1               5                   10                  15

Arg Gly Ser His Met Leu Glu Thr Glu Glu Glu Glu Glu Gly Ala
            20                  25                  30

Gly Ala Thr Leu Ser Arg Gly Pro Ala Phe Pro Gly Met Gly Ser Glu
        35                  40                  45

Glu Leu Arg Leu Ala Ser Phe Tyr Asp Trp Pro Leu Thr Ala Glu Val
    50                  55                  60

Pro Pro Glu Leu Leu Ala Ala Gly Phe Phe His Thr Gly His Gln
65                  70                  75                  80

Asp Lys Val Arg Cys Phe Phe Cys Tyr Gly Gly Leu Gln Ser Trp Lys
                85                  90                  95

Arg Gly Asp Asp Pro Trp Thr Glu His Ala Lys Trp Phe Pro Gly Cys
            100                 105                 110

Gln Phe Leu Leu Arg Ser Lys Gly Gln Glu Tyr Ile Asn Asn Ile His
        115                 120                 125

Leu Thr His Ser Leu
    130
```

INHIBITORS OF IAP

The present invention relates to organic compounds useful for therapy and/or prophylaxis in a mammal, and in particular to inhibitors of IAP proteins useful for treating cancers.

Apoptosis or programmed cell death is a genetically and biochemically regulated mechanism that plays an important role in development and homeostasis in invertebrates as well as vertebrates. Aberrancies in apoptosis that lead to premature cell death have been linked to a variety of developmental disorders. Deficiencies in apoptosis that result in the lack of cell death have been linked to cancer and chronic viral infections (Thompson et al., (1995) Science 267, 1456-1462).

One of the key effector molecules in apoptosis are the caspases (cysteine containing aspartate specific proteases). Caspases are strong proteases, cleaving after aspartic acid residues and once activated, digest vital cell proteins from within the cell. Since caspases are such strong proteases, tight control of this family of proteins is necessary to prevent premature cell death. In general, caspases are synthesized as largely inactive zymogens that require proteolytic processing in order to be active. This proteolytic processing is only one of the ways in which caspases are regulated. The second mechanism is through a family of proteins that bind and inhibit caspases.

A family of molecules that inhibit caspases are the Inhibitors of Apoptosis (IAP) (Deveraux et al., J Clin Immunol (1999), 19:388-398). IAPs were originally discovered in baculovirus by their functional ability to substitute for P35 protein, an anti-apoptotic gene (Crook et al. (1993) J Virology 67, 2168-2174). IAPs have been described in organisms ranging from Drosophila to human. Regardless of their origin, structurally, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion (Hinds et al., (1999) Nat. Struct. Biol. 6, 648-651). It is the BIR domain that is believed to cause the anti-apoptotic effect by inhibiting the caspases and thus inhibiting apoptosis. As an example, human X-chromosome linked IAP (XIAP) inhibits caspase 3, caspase 7 and the Apaf-1-cytochrome C mediated activation of caspase 9 (Deveraux et al., (1998) EMBO J. 17, 2215-2223). Caspases 3 and 7 are inhibited by the BIR2 domain of XIAP, while the BIR3 domain of XIAP is responsible for the inhibition of caspase 9 activity. XIAP is expressed ubiquitously in most adult and fetal tissues (Liston et al, Nature, 1996, 379(6563):349), and is overexpressed in a number of tumor cell lines of the NCI 60 cell line panel (Fong et al, Genomics, 2000, 70:113; Tamm et al, Clin. Cancer Res. 2000, 6(5):1796). Overexpression of XIAP in tumor cells has been demonstrated to confer protection against a variety of pro-apoptotic stimuli and promotes resistance to chemotherapy (LaCasse et al, Oncogene, 1998, 17(25):3247). Consistent with this, a strong correlation between XIAP protein levels and survival has been demonstrated for patients with acute myelogenous leukemia (Tamm et al, supra). Down-regulation of XIAP expression by antisense oligonucleotides has been shown to sensitize tumor cells to death induced by a wide range of pro-apoptotic agents, both in vitro and in vivo (Sasaki et al, Cancer Res., 2000, 60(20):5659; Lin et al, Biochem J., 2001, 353:299; Hu et al, Clin. Cancer Res., 2003, 9(7):2826). Smac/DIABLO-derived peptides have also been demonstrated to sensitize a number of different tumor cell lines to apoptosis induced by a variety of pro-apoptotic drugs (Arnt et al, J. Biol. Chem., 2002, 277(46):44236; Fulda et al, Nature Med., 2002, 8(8):808; Guo et al, Blood, 2002, 99(9):3419; Vucic et al, J. Biol. Chem., 2002, 277(14): 12275; Yang et al, Cancer Res., 2003, 63(4):831).

Melanoma IAP (ML-IAP) is an IAP not detectable in most normal adult tissues but is strongly upregulated in melanoma (Vucic et al., (2000) Current Bio 10:1359-1366). Determination of protein structure demonstrated significant homology of the ML-IAP BIR and RING finger domains to corresponding domains present in human XIAP, C-IAP1 and C-IAP2. The BIR domain of ML-IAP appears to have the most similarities to the BIR2 and BIR3 of XIAP, C-IAP1 and C-IAP2, and appears to be responsible for the inhibition of apoptosis, as determined by deletional analysis. Furthermore, Vucic et al., demonstrated that ML-IAP could inhibit chemotherapeutic agent induced apoptosis. Agents such as adriamycin and 4-tertiary butylphenol (4-TBP) were tested in a cell culture system of melanomas overexpressing ML-IAP and the chemotherapeutic agents were significantly less effective in killing the cells when compared to a normal melanocyte control. The mechanism by which ML-IAP produces an anti-apoptotic activity is in part through inhibition of caspase 3 and 9. ML-IAP did not effectively inhibit caspases 1, 2, 6, or 8.

Since apoptosis is a strictly controlled pathway with multiple interacting factors, the discovery that IAPs themselves are regulated was not unusual. In the fruit fly Drosophila, the Reaper (rpr), Head Involution Defective (hid) and GRIM proteins physically interact with and inhibit the anti-apoptotic activity of the Drosophila family of IAPs. In the mammal, the proteins SMAC/DIABLO act to block the IAPs and allow apoptosis to proceed. It was shown that during normal apoptosis, SMAC is processed into an active form and is released from the mitochondria into the cytoplasm where it physically binds to IAPs and prevents the IAP from binding to a caspase. This inhibition of the IAP allows the caspase to remain active and thus proceed with apoptosis. Interestingly, sequence homology between the IAP inhibitors shows that there is a four amino acid motif in the N-terminus of the processed, active proteins. This tetrapeptide appears to bind into a hydrophobic pocket in the BIR domain and disrupts the BIR domain binding to caspases (Chai et al., (2000) Nature 406:855-862, Liu et al., (2000) Nature 408:1004-1008, Wu et al., (2000) Nature 408 1008-1012).

SUMMARY OF THE INVENTION

In one aspect of the present invention there are provided novel inhibitors of IAP proteins having the general formula (I)

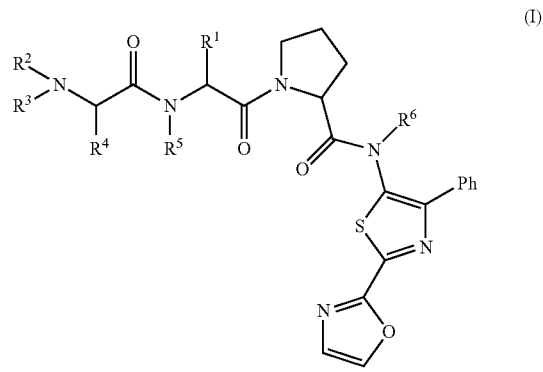

wherein
R$^1$ is C$_{3-7}$ cycloalkyl,
Ph is phenyl,
R$^2$, R$^3$, R$^4$, R$^5$, and R$^6$ are each independently in each occurrence H or C$_{1-6}$ alkyl; or,
a pharmaceutically acceptable salt thereof.
Formula I includes all stereoisomers.

In another aspect of the invention, there are provided compositions comprising compounds of formula I and a carrier, diluent or excipient.

In another aspect of the invention, there is provided a method of inducing apoptosis in a cell comprising introducing into said cell a compound of formula I.

In another aspect of the invention, there is provided a method of sensitizing a cell to an apoptotic signal comprising introducing into said cell a compound of formula I.

In another aspect of the invention, there is provided a method for inhibiting the binding of an IAP protein to a caspase protein comprising contacting said IAP protein with a compound of formula I.

In another aspect of the invention, there is provided a method for treating a disease or condition associated with the overexpression of an IAP protein in a mammal, comprising administering to said mammal an effective amount of a compound of formula I.

In another aspect of the invention, there is provided a method for treating cancer.

Figure 1:
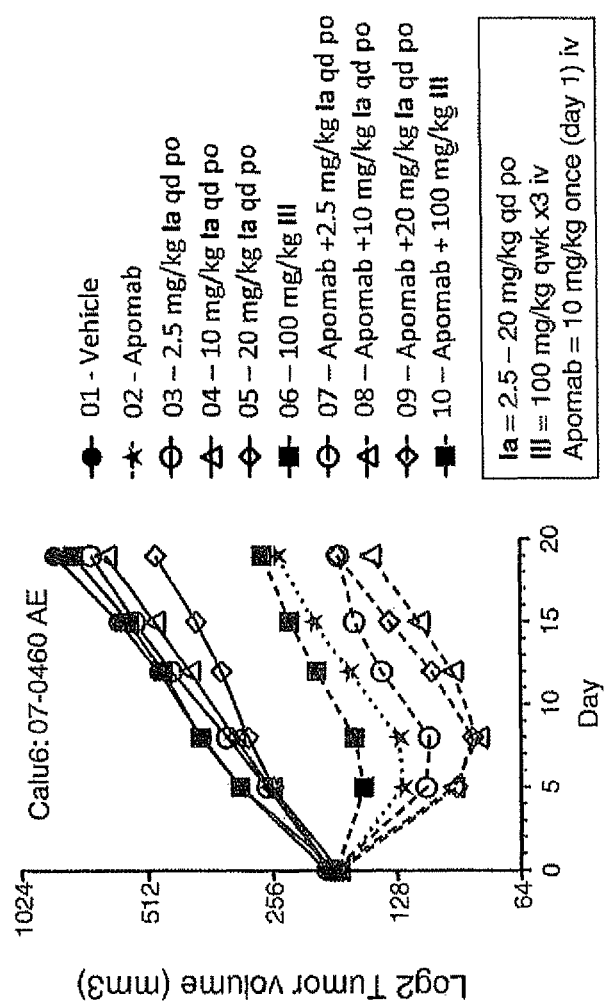
FIG. 1 shows the efficacy of Ia alone, as well as in combination with Apomab, along with efficacy data for prior art compound III alone and in combination with Apomab, in the Xenograft Model using Calu-6 lung adenocarcinoma cells. Ia was administered p.o. III was administered i.v. The doses were selected to produce the maximum tolerated dose of the drug.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—⇌—C(—OH)=CH—), amide/imidic acid (—C(=O)—NH—⇌—C(—OH)=N—) and amidine (—C(=NR)—NH—⇌—C(—NHR)=N—) tautomers. The latter two are particularly common in heteroaryl and heterocyclic rings. The present invention encompasses all tautomeric forms of the compounds described herein.

"Alkyl" means a branched or unbranched saturated aliphatic hydrocarbon group having up to 6 carbon atoms unless otherwise specified, also when used as part of another term, for example "alkylamino." Examples of preferred alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, and the like. The terms "lower alkyl" "C$_1$-C$_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl.

Cycloalkyl groups can be mono-, bi-, or tricyclic aliphatic rings of 3 to 7 carbon atoms. Preferred groups include cyclopropyl, cyclobutyl, cyclopentyl and cyclohexyl groups and more preferred are cyclopropyl and cyclohexyl and most preferred is cyclohexyl.

"Amino-protecting group" refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Preferred amino protecting groups are Boc, Fmoc and Cbz. Further examples of these groups are found in T. W. Greene and P. G. M. Wuts, "Protective Groups in Organic Synthesis", 2$^{nd}$ ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T.W. Greene, "Protective Groups in Organic Synthesis", John Wiley and Sons, New York, N.Y., 1981. The term "protected amino" refers to an amino group substituted with one of the above amino-protecting groups. These groups can be used during synthesis.

"Carboxy-protecting group" refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as LiAlH$_4$. (Such harsh removal conditions are also to be avoided when removing amino-protecting groups and hydroxy-protecting groups. Preferred carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", 2$^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T.W. Greene, "Protective Groups in Organic Synthesis", John Wiley and Sons, New York, N.Y., 1981, Chapter 5. The term "protected carboxy" refers to a carboxy group substituted with one of the above carboxy-protecting groups. These groups can be used during synthesis.

"Hydroxy-protecting group" refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", 2$^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T.W. Greene, "Protective Groups in Organic Synthesis", John Wiley and Sons, New York, N.Y., 1981. The term "protected hydroxy" refers to a hydroxy group substituted with one of the above hydroxy-protecting groups. These groups can be used during synthesis.

"Inhibitor" means a compound which reduces or prevents the binding of IAP proteins to caspase proteins or which reduces or prevents the inhibition of apoptosis by an IAP protein (e.g., c-IAP1, c-IAP2, X-IAP or ML-IAP). Alternatively, "inhibitor" means a compound which prevents the binding interaction of X-IAP with caspases or the binding interaction of ML-IAP with SMAC.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine. Formula I is also intended to encompass hydrates and solvates of the compounds.

The present invention provides novel compounds having the general formula I,

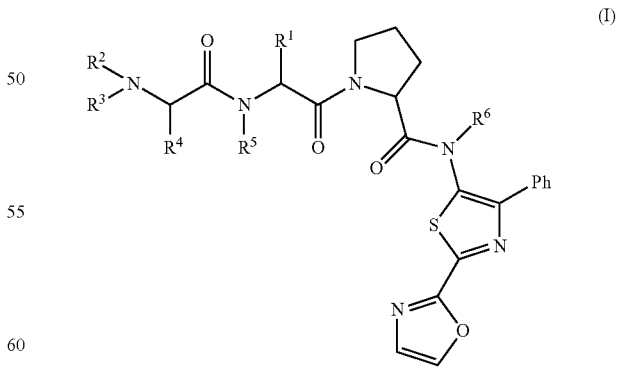

In a specific embodiment, $R^1$ is cyclohexyl. In another specific embodiment, $R^1$ is cyclopentyl. In a particular embodiment, $R^1$ is oriented such that the amino acid, or amino acid analogue, which it comprises is in the L-configuration.

$R^2$ and $R^3$ are independently H or $C_{1-6}$ alkyl. In one embodiment $R^2$ and $R^3$ are both H. In another embodiment $R^2$ is methyl and $R^3$ is H.

$R^4$ is H or $C_{1-6}$ alkyl. In a specific embodiment $R^4$ is H or methyl. In another embodiment $R^4$ is methyl. In another embodiment $R^4$ is oriented such that the amino acid, or amino acid analogue, which it comprises is in the L-configuration.

$R^5$ and $R^6$ are each independently H or $C_{1-6}$ alkyl. In one embodiment, $R^5$ and $R^6$ are H or methyl. In one embodiment, $R^5$ is H and $R^6$ is methyl. In another embodiment, $R^5$ is methyl and $R^6$ is H. In another embodiment $R^5$ and $R^6$ are both methyl. In another embodiment, $R^5$ and $R^6$ are both H.

In another aspect of the present invention the compound according to formula I is (S)-1-[(S)-2-cyclohexyl-2-((S)-2-methylamino-propionylamino)-acetyl]-pyrrolidine-2-carboxylic acid (2-oxazol-2-yl-4-phenyl-thiazol-5-yl)-amide (Ia).

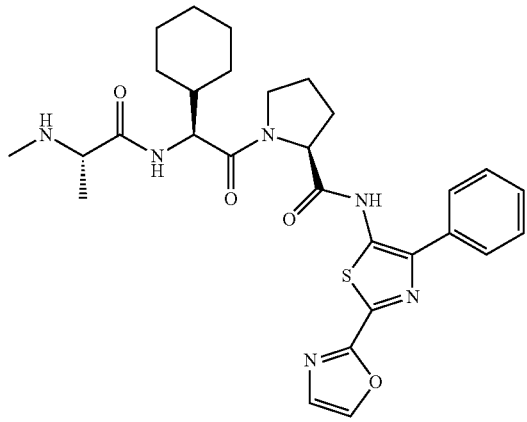 [SMILES: CN[C@@H](C)C(=O)N[C@H](C(=O)N1CCC[C@H]1C(=O)Nc1sc(-c2ncco2)nc1-c1ccccc1)C1CCCCC1]

Compounds of the invention contain one or more asymmetric carbon atoms. Accordingly, the compounds may exist as stereoisomers, including diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention. Preferably, compounds of the invention have the following stereochemical configuration of formula Ib wherein $R^1$, $R^2$, $R^3$, $R^5$ and $R^6$ are as described herein.

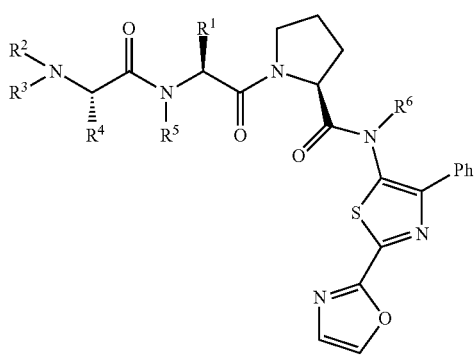

Compounds of formula II wherein A is an optionally substituted 5-member heterocycle comprising 1 to 4 heteroatoms have been disclosed in US Publication No. 20060014700. In some compounds disclosed in this publication A is N-(4-phenylthiazol-5-yl).

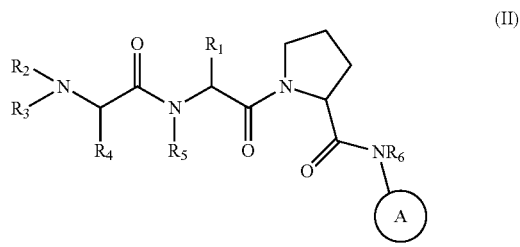

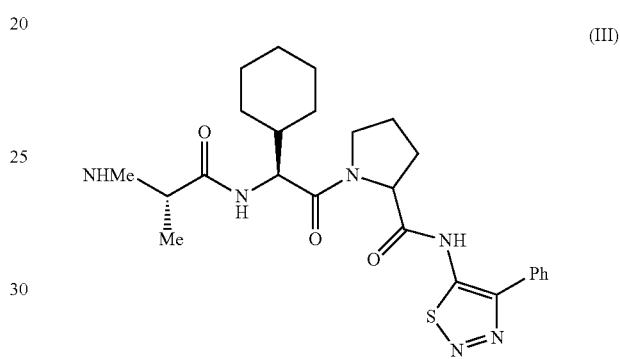

Figure 2:
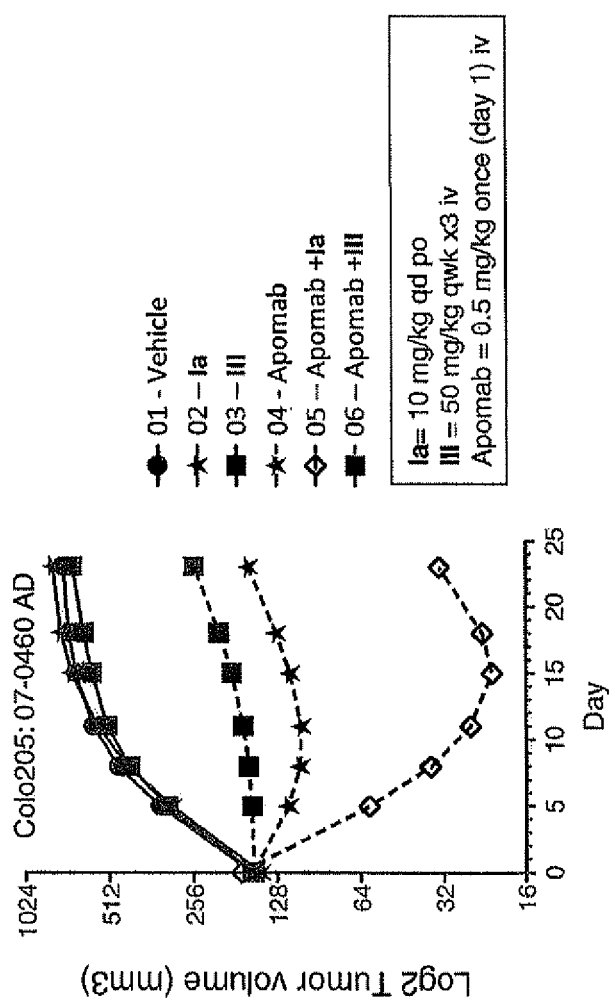
FIG. 2 shows the efficacy of Ia alone, as well as in combination with Apomab, along with efficacy data for prior art compound III alone and in combination with Apomab, in the Xenograft Model using Colo205 colorectal adenocarcinoma cells. Ia was administered p.o. III was administered i.v. The doses were selected to produce the maximum tolerated dose of the drug.

It has now been found that compounds wherein A is 2-(oxazol-2-yl)-4-phenylthiazol-5-yl per the invention afford an unexpected increase in potency and oral bioavailability. In addition, the compounds of the invention have generally lower side effects, including improved lung toxicity, e.g., compared to compound III a compound disclosed in US Publication No. 20060014700. FIGS. 1 and 2 show a comparative activity in xenograft tumor models between iv administration of III, compared to compound Ia of the present invention administered orally.

Synthesis

Compounds of the invention are prepared using standard organic synthetic techniques from commercially available starting materials and reagents. General techniques are disclosed in WO 98/46576 and U.S. Pat. No. 7,244,851, which are incorporated by reference herein for the preparation methods disclosed therein. It will be appreciated that synthetic procedures employed in the preparation of compounds of the invention will depend on the particular substituents present in a compound and that various protection and deprotection may be required as is standard in organic synthesis. In a general synthetic scheme compounds of the invention may be prepared using typical peptide chemistry techniques by coupling the amino acid residue analogues with typical amide coupling procedures. In scheme 1, amine-protected amino acid residue analogues are coupled and deprotected sequentially to give the final compounds using peptide synthesis protocols.

Scheme 1

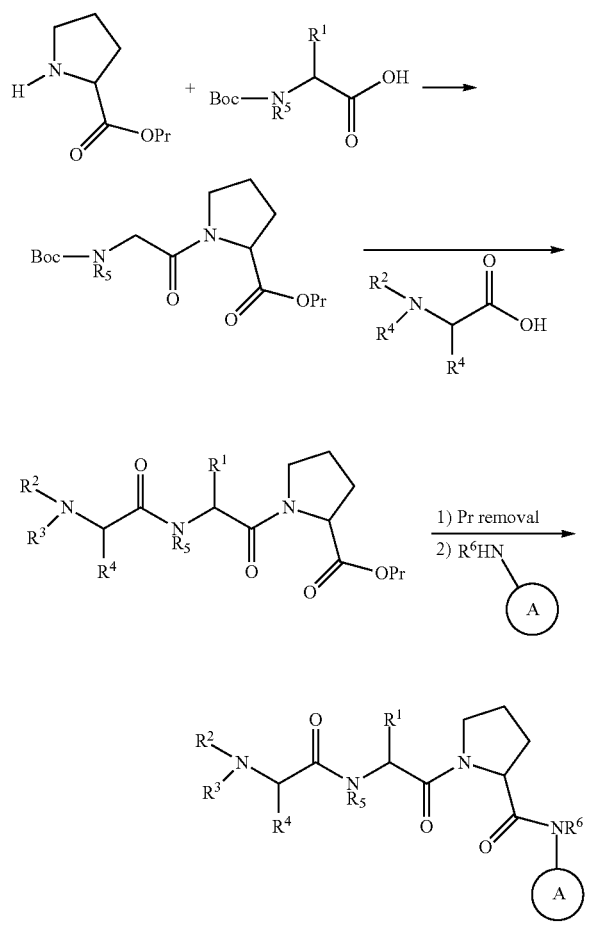

It will be appreciated that the amino acid analogs may be coupled in any order and may be prepared using solid phase support which is routine in the art.

When compounds of the invention incorporate $R^2$ or $R^3$ substituents other than H, they may also be prepared by substitution of a suitable acid intermediate which incorporates a leaving group with a desired amine. For example Br—CH($R^4$)—C(O)—OH is substituted with an amine $R^2$—NH$_2$ or $R^2$—NH—$R^3$ according to scheme 2.

Scheme 2

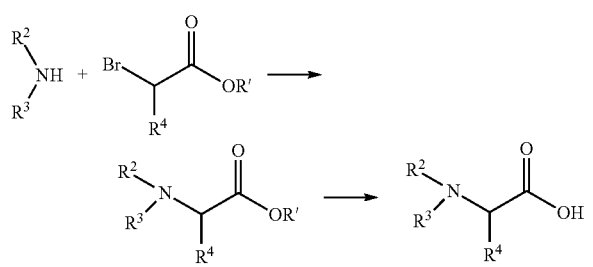

Alternatively, the substitution reaction introducing $R^2$ or $R^3$ substituents may be performed as a final step in the preparation of the compound as illustrated in scheme 3.

Scheme 3

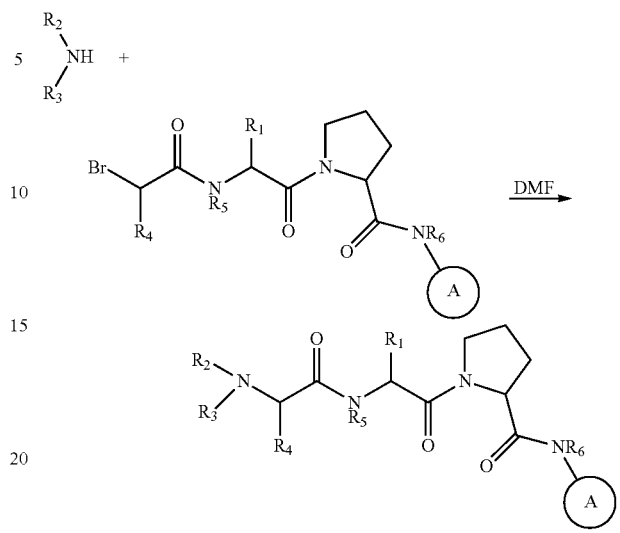

In a particular embodiment, 2-bromopropionic acid is reacted with the appropriate amines dissolved in DMF and bubbled until substitution is complete to form N-substituted alanine residue.

Amine substituted ring A compounds which serve as an intermediate for preparing compounds of the invention are commercially available or else are prepared from commercially available reagents employing standard organic chemistry techniques. 2-(Oxazol-2-yl)-4-phenylthiazol-5-amine can be prepared by condensation of an α-aminophenylacetonitrile hydrochloride and oxazole-2-carbaldehyde in the presence of sulfur and TEA (Scheme 4).

Scheme 4

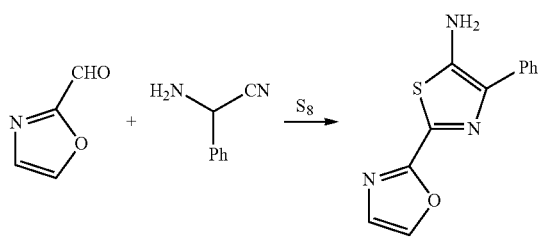

UTILITY

The compounds of the invention inhibit the binding of IAP proteins to caspases, in particular X-IAP binding interaction with caspases 3 and 7. The compounds also inhibit the binding of ML-IAP to Smac protein. Accordingly, the compounds of the invention are useful for inducing apoptosis in cells or sensitizing cells to apoptotic signals, in particular cancer cells. Compounds of the invention are useful for inducing apoptosis in cells that overexpress IAP proteins (e.g., c-IAP1, c-IAP2, X-IAP or ML-IAP). Alternatively, compounds of the invention are useful for inducing apoptosis in cells in which the mitochondrial apoptotic pathway is disrupted such that release of Smac from ML-IAP proteins is inhibited, for example by up regulation of Bcl-2 or down regulation of Bax/Bak. More broadly, the compounds can be used for the treatment of cancer.

They are especially useful for the treatment of all cancer types which fail to undergo apoptosis. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma. Useful is treatment of solid tumors. Useful also is treatment of breast cancer, pancreatic adenocarcinoma or malignant melanoma.

Compounds of the invention are useful for sensitizing cells to apoptotic signals. Accordingly, the compounds may be administered prior to, concomitantly with, or following administration of radiation therapy or cytostatic or antineoplastic chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a preferred embodiment, compounds of the present invention are coadministered with a cytostatic compound selected from the group consisting of cisplatin, doxorubicin, paclitaxel, docetaxel and mitomycin C. Most preferred, the cytostatic compound is doxorubicin. Useful are combinations with 5-FU, gemcitabine, capecitabine, vinorelbine, bevacizumab, or taxanes.

Another class of active compounds which can be used in the present invention are those which are able to sensitize for or induce apoptosis by binding to death receptors ("death receptor agonists"). Such agonists of death receptors include death receptor ligands such as tumor necrosis factor a (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. Preferably, the death receptor ligand is TNF-α. More preferably the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

More generally, the compounds of the invention can be used in combination therapy. "Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

Thus, in one aspect of the invention, the subject compounds may be administered in combination with one or more separate agents that modulate protein kinases involved in various disease states or targets downstream thereof. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R, PI3K, AKT, mTor); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g. HSP90), hedgehog inhibitors and proteosomes.

In a preferred embodiment, subject compounds may be combined with antineoplastic agents (e.g. small molecules, monoclonal antibodies, antisense RNA, and fusion proteins) that inhibit one or more biological targets such as Erivedge, Zolinza, Tarceva, Iressa, Tykerb, Gleevec, Sutent, Sprycel, Nexavar, CNF2024, RG108, BMS387032, Affinitak, Avastin, Herceptin, Erbitux, AG24322, PD325901, ZD6474, PD184322, Obatodax, ABT737 and AEE788. Also included are monoclonal antibodies directed toward specific kinases and/or receptors, e.g., those mentioned herein and others. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents (some of which are also discussed above) include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloidssuch asPodophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumabozogamicin, Rituximab, Trastuzumab, IbritumomabTioxetan, Cetuximab, Panitumumab, Tositumomab, Bevacizumab); and miscellaneous anti-neoplastics such as ribonucleotidereductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA), etc.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to treat the target diseases, e.g., to inhibit IAP interaction with caspases, induce apoptosis or sensitize a malignant cell to an apoptotic signal. Such amount is preferably below the amount that is toxic to normal cells, or the mammal as a whole.

Generally, the compounds of this invention can be dosed once or multiple times daily. They can also be dosed on a continuous daily schedule without treatment breaks. They can also be thus dosed with treatment breaks. These options are also available when used with other agents or modalities. The initial pharmaceutically effective amount of the compound of the invention administered parenterally per dose will be in the range of about 0.01-100 mg/kg, preferably about 0.1 to 20 mg/kg of patient body weight per day, with the typical initial range of compound used being 0.3 to 15 mg/kg/day. Oral unit dosage forms, such as tablets and capsules, preferably contain from about 25 to about 1000 mg of the compound of the invention. Oral administration is preferred. On/Off dosing schedules can be used as are common for cancer treatments, e.g., daily oral dosing for 1, 2, 3, 4, etc., weeks, followed by a treatment break of 1, 2, etc., weeks, followed by daily oral dosing for 1, 2, 3, 4, etc., weeks, etc. In a preferred option, the compounds of the invention are dosed daily in a range of about 25 to about 3000 mg per day, more preferably about 300 to about 1500 mg of compound per day.

The compound of the invention may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants.

More generally, the compounds of this invention can be used in accordance with the disclosure given in WO 98/46576 and U.S. Pat. No. 7,244,851, whose disclosures are incorporated by reference herein for their general guidance on how to use the compounds.

EXAMPLES

The invention will be more fully understood by reference to the following examples. They should not, however, be construed as limiting the scope of the invention. Abbreviations used herein are as follows:
ACN: acetonitrile;
Chg: cyclohexylglycine;
DCM: dichloromethane
DIPEA: diisopropylethylamine;
DMAP: 4-dimethylaminopyridine;
DME: 1,2-dimethoxyethane;
DMF: dimethylformamide;
DMSO: dimethylsulfoxide
EDC: 1-ethyl-3-(3-dimethylaminopropyl)carbodiimide;
EEDQ: 2-ethoxy-1-ethoxycarbonyl-1,2-dihydroquinoline
LCMS: liquid chromatography mass spectrometry;
HATU: O-(7-Azobenzotriazol-1-yl)-1,1,3,3-tetramethyluronium hexafluorophosphate;
HOBt: N-Hydroxybenzotriazole
HBTU: 2-(1H-Benzotriazol-1-yl)-1,1,3,3-Tetramethyluronium Hexafluorophosphate
HPLC: high performance liquid chromatography;
NBS: N-bromosuccinamide;
TASF: tris(dimethylamino)sulfonium difluorotrimethylsilicate;
TEA: triethylamine;
TFA: trifluoroacetate;
THF: tetrahydrofuran;

Referential Example 1

1-[2-Cyclohexyl-2-(2-methylamino-propionylamino)-acetyl]-pyrrolidine-2-carboxylic acid (2-phenyl-2H-pyrazol-3-yl)-amide A solution of Boc-MeAla-Chg-Pro-OH (47.0 mg, 0.107 mmol) and pyridine (26 μL, 0.32 mmol) in anhydrous dichloromethane (300 μL) was cooled to 0° C. and a solution of oxalyl chloride in dichloromethane (54 μL, 2.0 M, 0.11 mmol) was added dropwise over 10 minutes. The mixture was stirred at 0° C. for 15 minutes, then at ambient temperature for 45 minutes, and a solution of 5-amino-1-phenylpyrazole (15.9 mg, 0.100 mmol; TCI America catalog # A0174) and pyridine (15.5 μL, 0.191 mmol) in dichloromethane (0.5 mL) was added. The resulting mixture was stirred at ambient temperature for 16 hours, diluted with dichloromethane to 20 mL, and washed with 0.2 N aqueous sodium hydroxide (20 mL). The organic phase was dried (MgSO$_4$) and concentrated under reduced pressure. The crude product was purified by column chromatography (silica gel, 60% ethyl acetate in hexanes, then 100% ethyl acetate) to yield a yellow oil: m/z 581 (M+H$^+$). The oil was treated with 5% trifluoroacetic acid in dichloromethane (2 mL), and after 18 hours the solvent was removed in vacuo. The resulting oil (29.3 mg, 57% yield over 2 steps) was further purified by reversed-phase HPLC to yield the product (TFA salt, 9.6 mg, 15% yield): m/z 481 (M+H$^+$), 503 (M+Na$^+$).

Referential Example 2

Acid Fluoride Coupling Procedure

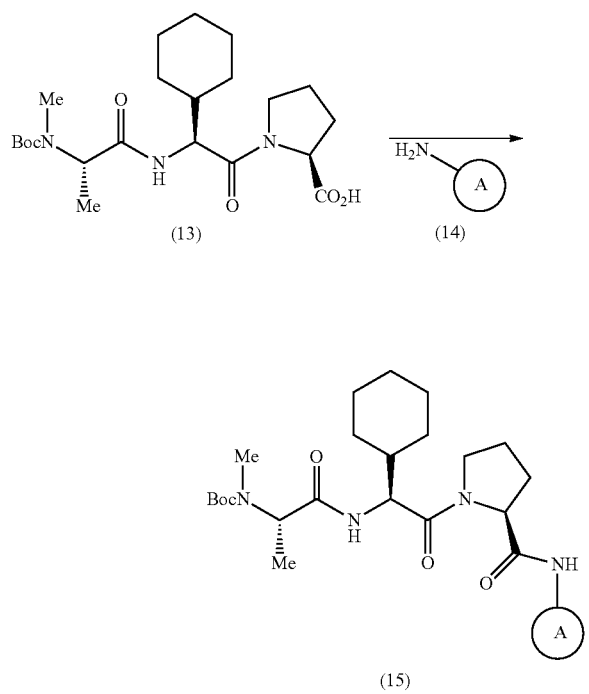

A solution of Boc-MeAla-Chg-Pro-OH (2.3 mmol) and pyridine (6.9 umol) in anhydrous DCM (23 ml) was cooled to 0° C. and cyanuric fluoride (2.3 mmol) added dropwise over 30 sec. The mixture was stirred at 0° C. for 15 min, at RT for 5 h, and then quenched with water. The mixture was extracted three times with DCM (total 100 ml), and the combined organic phases washed with brine and dried (Na$_2$SO$_4$). Filtration and concentration in vacuo yielded the peptide acid fluoride as a clear, colorless oil used directly without further purification.

A solution of the crude acid fluoride (0.50 mmol) and pyridine (1.5 mmol) in DCM (2.5 ml) was added to the solid amine (14, 0.50 mmol), and the resulting mixture stirred either at RT or at 50° C. (sealed vessel). The mixture was poured into aqueous NaHCO$_3$ and then extracted three times with dichloromethane (total 100 ml). The combined organic phases were washed with brine, dried (Na$_2$SO$_4$), filtered and concentrated in vacuo. The crude peptide amide was used directly without further purification.

Referential Example 3

1-[2-Cyclohexyl-2-(2-methylamino-propionylamino)-acetyl]-pyrrolidine-2-carboxylic acid (4-phenyl-[1,2,3]thiadiazol-5-yl)-amide

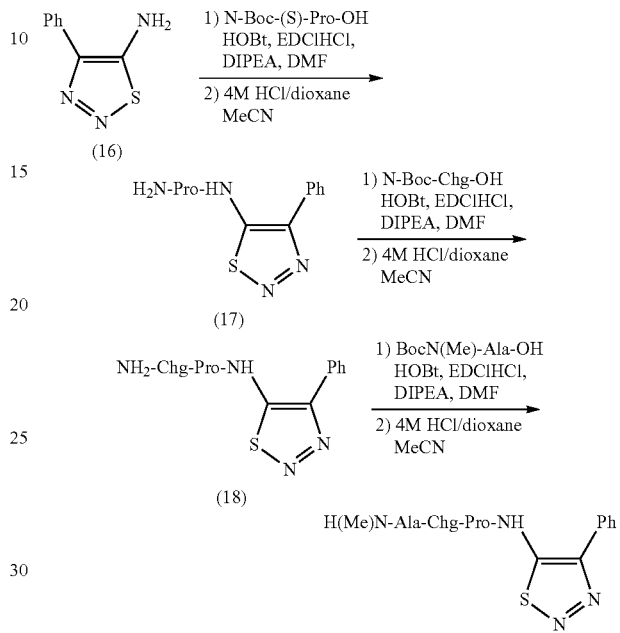

step 1: To a solution of Boc-L-Pro-OH (2 eq), HOBt (1.9 eq), EDC-HCl (1.9 eq) and DIPEA (5 eq) in DMF (10-15 vol) was added 4-phenyl-1,2,3-thiadiazol-5-amine (16). The reaction, initially mildly exothermic, was heated to 75° C. and stirred overnight, cooled to RT and the DMF was partially removed in vacuo. The solution was diluted with EtOAc (10-15 vol) followed by washing with 1M HCl (2×), NaHCO$_3$ (1×), and brine (1×) (1:1 aq/org). The organic layer was concentrated in vacuo and the resulting solid was slurried in refluxing MeCN (a minimum volume necessary for easy stirring) for 30 min and then cooled to RT. Suction filtration gave Boc-protected conjugation product as an off-white crystalline solid in ca. 77% yield. The Boc-protected product was suspended in a solution of 4M HCl/dioxane (4-5 eq acid) and MeCN (1 vol eq to the dioxane solution) and stirred at RT until LCMS indicated complete deprotection (ca. 1 h). The reaction mixture was concentrated in vacuo and the resulting solid was vigorously slurried in refluxing MeCN (a minimum volume necessary for easy stirring), cooled to RT, and the solid collected by suction filtration and washed with cold MeCN until residual color was removed from the cake which afforded the HCl salt of (S)—N-(4-phenyl-1,2,3-thiadiazol-5-yl)pyrrolidine-2-carboxamide (17) as an off-white solid in approximately quantitative yield.

step 2: To a solution of 17 and DIPEA (5 eq) in DMF (10-15 vol) was added the Boc-L-Chg (1.5 eq), HOBt (1.4 eq) and EDC-HCl (1.4 eq). The reaction was stirred for ca 2 h then diluted with EtOAc (15 vol) and washed with 1M HCl (2×), NaHCO$_3$ (1×), and brine (1×) (1:1 aq/org). The organic extract was dried (Na$_2$SO$_4$), filtered and concentrated in vacuo. The resulting solid is slurried in EtOH/

Hexane (20:80) (a minimum volume necessary for easy stirring) and filtered to give Boc-protected conjugate product as a fluffy white solid in ca. 80% yield. The Boc-protected was dissolved in a solution of 4M HCl/dioxane (4-5 eq acid) and MeCN (0.25 volume eq to the dioxane solution) and stirred at RT for ca. 1 hr. The reaction was concentrated to dryness with toluene (2×) (the same volume as the deprotection solution) to yield the HCl salt of (S)-1-((S)-2-amino-2-cyclohexylacetyl)-N-(4-1,2,3-thiadiazol-5-yl)pyrrolidine-2-carboxamide (18) as a white crystalline solid in approximately quantitative yield.

step 3: To a solution of 18 and DIPEA (5 eq.) in DMF (10-15 vol) was added the Boc-L-N-methyl Ala (1.5 eq), HOBt (1.4 eq), and EDC-HCl (1.4 eq). The reaction was stirred for 1 h, diluted with EtOAc (15 vol) and washed with 1M HCl (2×), NaHCO$_3$ (1×), and brine (1×) (1:1 aq/org). The organic extract was dried (Na$_2$SO$_4$), filtered and concentrated in vacuo to give afford Boc-protected conjugate product as a beige, foamy solid in ca. 85% yield. The Boc-protected product was dissolved in a solution of 4M HCl/dioxane (4-5 eq acid) and MeCN (0.25 volume eq to the dioxane solution) and stirred at RT for ca. 1 hr. The reaction was concentrated to dryness with toluene (2×) (same volume as deprotection solution) and the resulting solid was slurried in a solution of MTBE/EtOAc (70:30) (minimal volume necessary for easy stirring), filtered and collected to yield crude (S)-1-((S)-2-cyclohexyl-2-((S)-2-(methylamino)propanamido)acetyl)-N-(4-phenyl-1,2,3-thiadiazol-5-yl)pyrrolidine-2-carboxamide (d) as an off-white free-flowing solid. The crude HCl salt was suspended in MeOH (4 vol minimum) and dissolved with stirring at 65° C. Warm isopropyl acetate (6-8 vol) was added in two portions, keeping the temperature at ca. 60° C. then the solution was allowed to cool with stirring. Crystallization took place rapidly, the suspension was stirred at RT for several hours, then stirred at 0° C. for an hour before the solid was collected by suction filtration. The crude product was washed with MeOH/iPrOAc (1:4, 2 vol) and dried to 19 as a white/off-white crystalline solid in ca. 80% yield.

Referential Example 4

5-Amino-2-(oxazol-2-yl)-4-phenylthiazole

A suspension of α-aminophenylacetonitrile hydrochloride (1.52 g, 8.99 mmol), powdered sulfur (289 mg, 9.01 mmol) and oxazole-2-carbaldehyde (873 mg, 8.99 mmol) in EtOH (18 mL) was treated with TEA (1.88 mL, 13.5 mmol), and the mixture stirred at 50° C. for 60 min. The cooled mixture was treated with aqueous hydroxylamine (1.00 ml, 50% wt, 15 mmol) at RT overnight, filtered and concentrated in vacuo. The residue was partitioned between EtOAc and aqueous NaHCO$_3$, and the separated organic phase washed with brine, dried (Na$_2$SO$_4$), filtered and concentrated in vacuo to a dark brown oil. The crude oil was preabsorbed onto SiO$_2$ and purified by automated flash chromatography eluting with a gradient of 5-70% ethyl acetate in hexanes to yield 5-amino-2-(oxazol-2-yl)-4-phenylthiazole (20, 159 mg, 7.3%).

Example 1

(S)-1-[(S)-2-Cyclohexyl-2-((S)-2-methylamino-propionylamino)-acetyl]-pyrrolidine-2-carboxylic acid (2-oxazol-2-yl-4-phenyl-thiazol-5-yl)-amide (Ia)

step 1: To a solution of Boc-L-Proline (4.5 g, 0.02 mmol) and pyridine (8.45 mL, 0.104 mmol) in DCM (20 mL) cooled in an ice bath was added dropwise cyanuric fluoride (5.35 mL, 0.0627 mmol). After the addition the reaction became milky. The solution was stirred at 0° C. for 10 min then warmed to RT and stirred for 4 h. The reaction was quenched with water, and thrice extracted with DCM. The combined organic extracts were washed with brine, dried, and concentrated in vacuo to afford tert-butyl 2-(fluorocarbonyl)pyrrolidine-1-carboxylate. The crude acid fluoride was used in next coupling reaction immediately.

The freshly prepared acid fluoride (4.55 g, 0.02 mmol) was dissolved in MeCN (20 mL), and treated with 20 (1.7 g, 0.007 mmol) and pyridine (2.82 mL, 0.035 mmol). The reaction was heated to 50° overnight. The reaction mixture was quenched with sat. NaHCO$_3$ and thrice extracted with EtOAc. The combined organic layers were washed with brine, dried and concentrated. The crude product was purified by SiO$_2$ chromatography eluting with an EtOAc/hexane gradient (50 to 80% EtOAc) to afford (S)-tert-butyl 2-(2-(oxazol-2-yl)-4-phenylthiazol-5-ylcarbamoyl)pyrrolidine-1-carboxylate (21).

Removal of the Boc protecting group and sequential coupling with BocHN-Chg-OH and H(Me)N-Ala-OH were carried out in accord with procedures in steps 2 and 3 of referential example 3. Purification of the Chg coupling product also was accomplished by SiO$_2$ chromatography eluting with an EtOAc/hexane gradient (50 to 80% EtOAc). The crude Boc-protected tripeptide product was purified by ISCO (50-80% EtOAc/Hexane). After remove of the Boc group the final product was purified by Prep HPLC to afford pure Ia: (M+H)$^+$=ms 565.3

Example 2

Other Compounds of this invention, e.g.,
1. (S)-1-[(S)-2-cyclopropyl-2-((S)-2-methylamino-propionylamino)-acetyl]-pyrrolidine-2-carboxylic acid (2-oxazol-2-yl-4-phenyl-thiazol-5-yl)-amide;
2. (S)-1-[(S)-2-cyclopentyl-2-((S)-2-methylamino-propionylamino)-acetyl]-pyrrolidine-2-carboxylic acid (2-oxazol-2-yl-4-phenyl-thiazol-5-yl)-amide;
3. (S)-1-[(S)-2-cycloheptyl-2-((S)-2-methylamino-propionylamino)-acetyl]-pyrrolidine-2-carboxylic acid (2-oxazol-2-yl-4-phenyl-thiazol-5-yl)-amide;
4. (S)-1-[(S)-2-cyclohexyl-2-((S)-2-ethylamino-propionylamino)-acetyl]-pyrrolidine-2-carboxylic acid (2-oxazol-2-yl-4-phenyl-thiazol-5-yl)-amide;
5. (S)-1-[(S)-2-cyclohexyl-2-((S)-2-methylamino-propionylamino)-acetyl]-pyrrolidine-2-carboxylic acid (2-oxazol-2-yl-4-phenyl-thiazol-5-yl)-N-methyl-amide; and
6. (S)-1-[(S)-2-cyclohexyl-2-((S)-2-methylamino-propionylamino)-2-methyl-acetyl]-pyrrolidine-2-carboxylic acid (2-oxazol-2-yl-4-phenyl-thiazol-5-yl)-amide, can be prepared analogously to the compound of Example 1 using correspondingly analogous starting materials in the procedure of Example 1.

Example 3

IAP Inhibition Assays

In the following experiments was used a chimeric BIR domain referred to as MLXBIR3SG in which 11 of 110 residues correspond to those found in XIAP-BIR3, while the remainder correspond to ML-IAP-BIR. The chimeric protein MLXBIR3SG was shown to bind and inhibit caspase-9 significantly better than either of the native BIR domains, but bound Smac-based peptides and mature Smac with affinities similar to those of native ML-IAP-BIR. The improved caspase-9 inhibition of the chimeric BIR domain MLXBIR3SG has been correlated with increased inhibition of doxorubicin-induced apoptosis when transfected into MCF7 cells.

MLXBIR3SG Sequence:

(SEQ ID NO.: 1)
MGSSHHHHHHSSGLVPRGSHMLETEEEEEEGAGATLSRGPAFPGMGSEEL
RLASFYDWPLTAEVPPELLAAAGFFHTGHQDKVRCFFCYGGLQSWKRGDD
PWTEHAKWFPGCQFLLRSKGQEYINNIHLTHSL

TR-FRET Peptide Binding Assay

Time-Resolved Fluorescence Resonance Energy Transfer competition experiments were performed on the Wallac Victor2 Multilabeled Counter Reader (Perkin Elmer Life and Analytical Sciences, Inc.) according to the procedures of Kolb et al (Journal of Biomolecular Screening, 1996, 1(4): 203). A reagent cocktail containing 300 nM his-tagged MLXBIR3SG; 200 nM biotinylated SMAC peptide (AVPI); 5 µg/mL anti-his allophycocyanin (XL665) (CISBio International); and 200 ng/mL streptavidin-europium (Perkin Elmer) was prepared in reagent buffer (50 mM Tris [pH 7.2], 120 mM NaCl, 0.1% bovine globulins, 5 mM DTT and 0.05% octylglucoside). (Alternatively, this cocktail can be made using europium-labeled anti-His (Perkin Elmer) and streptavidin-allophycocyanin (Perkin Elmer) at concentrations of 6.5 nM and 25 nM, respectively). The reagent cocktail was incubated at room temperature for 30 minutes. After incubation, the cocktail was added to 1:3 serial dilutions of an antagonist compound (starting concentration of 50 µM) in 384-well black FIA plates (Greiner Bio-One, Inc.). After a 90 minute incubation at room temperature, the fluorescence was read with filters for the excitation of europium (340 nm) and for the emission wavelengths of europium (615 nm) and a allophycocyanin (665 nm). Antagonist data were calculated as a ratio of the emission signal of allophycocyanin at 665 nm to that of the emission of europium at 615 nm (these ratios were multiplied by a factor of 10,000 for ease of data manipulation). The resulting values were plotted as a function of antagonist concentration and fit to a 4-parameter equation using Kaleidograph software (Synergy Software, Reading, Pa.). Indications of antagonist potency were determined from the IC50 values. Compounds of the invention where found to have IAP inhibitory activity which was demonstrated in this assay.

Fluorescence Polarization Peptide Binding Assay

Polarization experiments were performed on an Analyst HT 96-384 (Molecular Devices Corp.) according to the procedure of Keating, S. M., Marsters, J, Beresini, M., Ladner, C., Zioncheck, K., Clark, K., Arellano, F., and Bodary., S. (2000) in Proceedings of SPIE: In Vitro Diagnostic Instrumentation (Cohn, G. E., Ed.) pp 128-137, Bellingham, Wash. Samples for fluorescence polarization affinity measurements were prepared by addition of 1:2 serial dilutions starting at a final concentration of 5 µM of MLXBIR3SG in polarization buffer (50 mM Tris [pH 7.2], 120 mM NaCl, 1% bovine globulins 5 mM DTT and 0.05% octylglucoside) to 5-carboxyflourescein-conjugated AVPdi-Phe-NH$_2$ (AVP-diPhe-FAM) at 5 nM final concentration.

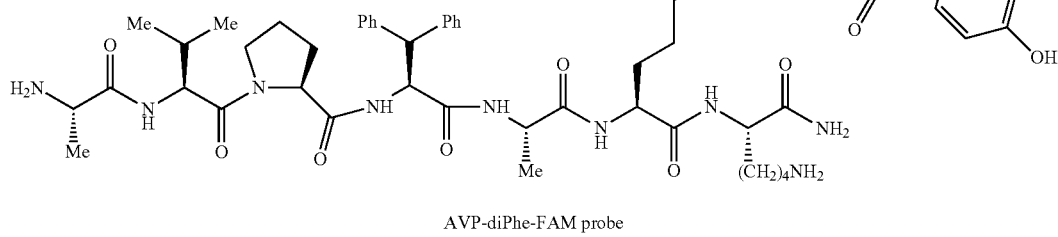

AVP-diPhe-FAM probe

The reactions were read after an incubation time of 10 minutes at room temperature with standard cut-off filters for the fluorescein fluorophore ($\lambda_{ex}$=485 nm; $\lambda_{em}$=530 nm) in 96-well black HE96 plates (Molecular Devices Corp.). Fluorescence values were plotted as a function of the protein concentration, and the IC50s were obtained by fitting the data to a 4-parameter equation using Kaleidograph software (Synergy software, Reading, Pa.). Competition experiments were performed by addition of the MLXBIR3SG at 30 nM to wells containing 5 nM of the AVP-diPhe-FAM probe as well as 1:3 serial dilutions of antagonist compounds starting at a concentration of 300 µM in the polarization buffer. Samples were read after a 10-minute incubation. Fluorescence polarization values were plotted as a function of the antagonist concentration, and the IC$_{50}$ values were obtained by fitting the data to a 4-parameter equation using Kaleidograph software (Synergy software, Reading, Pa.). Inhibition constants (K$_i$) for the antagonists were determined from the IC$_{50}$ values. Compounds of the invention where found to have IAP inhibitory activity which was demonstrated in this assay. For example, the value for K$_i$ for compound Ia is 0.014 (ML-IAP-BIR).

Example 4

Tumor Xenograft Studies (FIGS. 1 and 2)

All procedures involving animals were performed in accordance with the guidelines of the Genentech Institutional Animal Care and Use Committee. Cancer cells such as Human breast MDA-MB-231, colorectal, Colo205, or NSCLC, Calu6 cancer cells were obtained from American Type Culture Collection (Manassas, Va.). Cells were resuspended in HBSS (Colo205) or the cell suspension was mixed 1:1 with Matrigel (BD Biosciences; MDA-MB-231, Calu6). The cells ($1.5 \times 10^7$ for MDA-MB-231; $5.0 \times 10^7$ for Colo205, Calu6) were then implanted subcutaneously into the right flank of female nude mice (Charles River Laboratories, Hollister, Calif.) aged 6-8 weeks. Tumor volumes were calculated using the mean diameter measured with vernier calipers using the formula $v=0.5 \times a \times b^2$, were a and b are the largest and smallest perpendicular tumor diameters, respectively. Ten mice with the appropriate mean tumor volume were assigned randomly to each of six groups. The mean tumor volume ± the standard error of the mean (SEM) for all six groups was 168±3 mm$^3$ at the initiation of treatment (Day 0). The mice were observed on each day of the study, and tumor volumes and body weights were measured twice each week. Percent tumor growth inhibition was calculated using the formula % TGI=100×(1−Tumor Volume$_{dose}$/Tumor Volume$_{vehicle}$).

In this assay using human breast MDA-MB-231●X1 cells, Compound Ia of the invention has an MED value of 3.4 mg/kg (iv Qwk). This is five times less than the amount needed for prior art compound III in the same assay under the same conditions (MED=18.6 mg/kg). The AUC for Ia is four times less than that for III for similar efficacy.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A method for preparing a compound of formula I

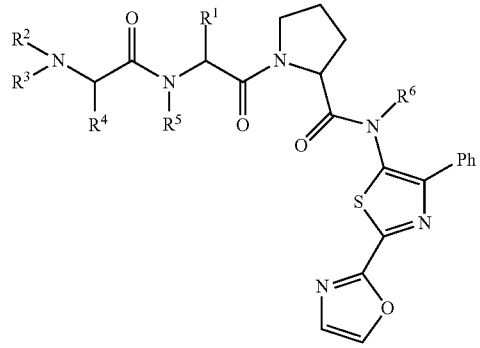

wherein
Ph is phenyl;
$R^1$ is $C_{3-7}$ cycloalkyl;
$R^2$, $R^3$, $R^4$, $R^5$, and $R^6$ are each independently in each occurrence H or $C_{1-6}$ alkyl; or
a pharmaceutically acceptable salt thereof;
which comprises:
coupling an amine-protected amino acid residue and deprotecting it according to the following Scheme 1:

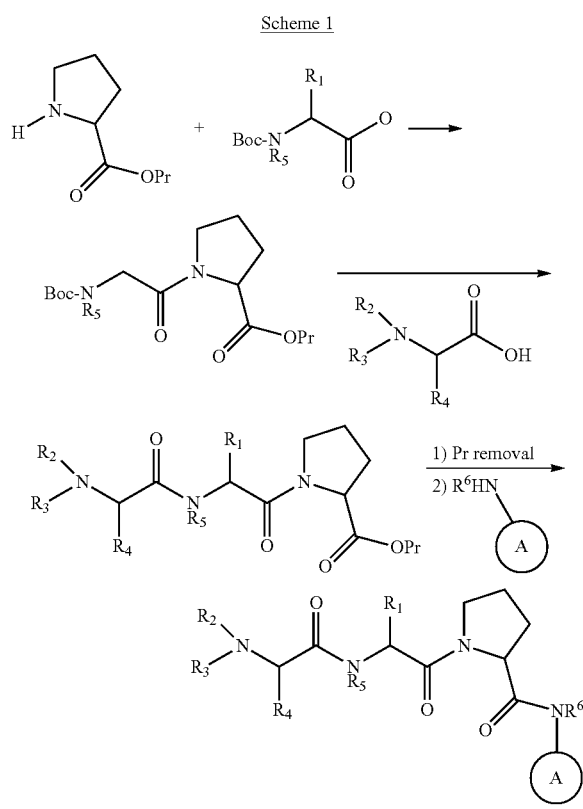

or by a substitution reaction according to Scheme 3:

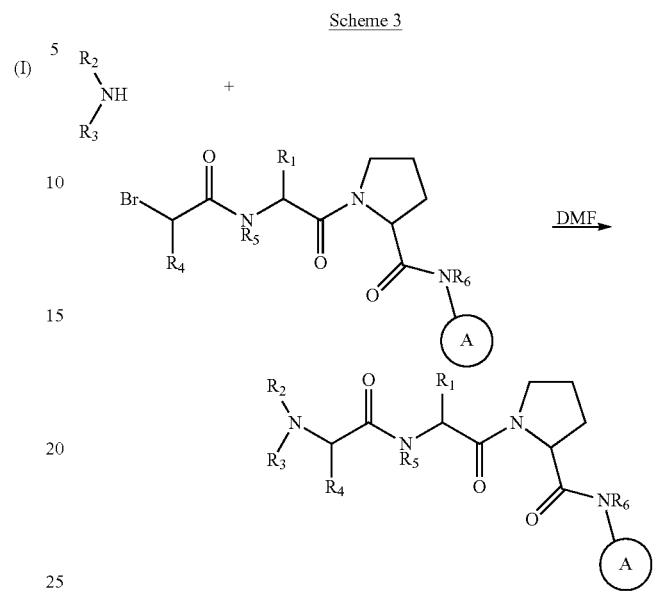

wherein the A ring is the oxazole-phenylthiazole group shown in formula (I), Pr is a carboxy-protecting group, Br is bromine and DMF is dimethylformamide.

2. The method of claim 1 wherein the compound prepared is (S)-1-[(S)-2-cyclohexyl-2-((S)-2-methylamino-propionylamino)-acetyl]-pyrrolidine-2-carboxylic acid (2-oxazol-2-yl-4-phenyl-thiazol-5-yl)-amide (Ia) or a pharmaceutically acceptable salt thereof.

3. The method of claim 1 wherein $R^2$-$R^6$ are each independently H or methyl.

4. The method of claim 1 wherein $R^1$ is cyclohexyl.

5. The method of claim 3 wherein $R^1$ is cyclohexyl.

6. The method of claim 3 wherein one of $R^2$ and $R^3$ is H and the other is methyl; or $R^4$ is methyl; or $R^5$ and $R^6$ are each H.

7. The method of claim 1, wherein the amino acid residue is provided on a solid phase support.

8. The method of claim 1, wherein, when $R^2$ or $R^3$ are substituents other than H, the method further comprises the following Scheme 2 to prepare the reactant used in the second step of Scheme 1:

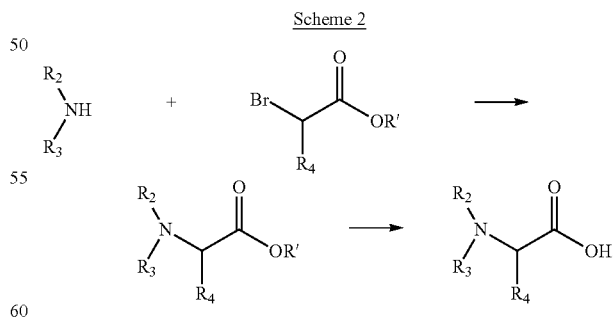

9. The method of claim 8, wherein 2-bromopropionic acid is reacted with the an amine dissolved in DMF and bubbled until substitution is complete to form the N-substituted alanine residue.

10. The method of claim 1, further comprising preparing the A ring reactant used in the third step of Scheme 1 by condensation of an α-aminophenylacetonitrile hydrochloride and oxazole-2-carbaldehyde in the presence of sulfur and TEA according to Scheme 4:
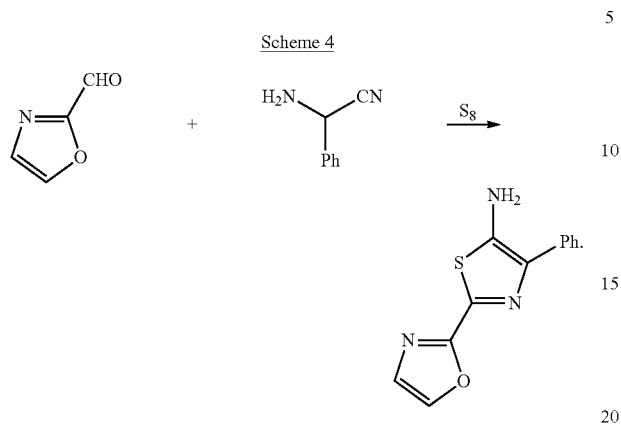
* * * * *